(12) United States Patent
Mahood et al.

(10) Patent No.: US 12,329,674 B2
(45) Date of Patent: Jun. 17, 2025

(54) COLLECTING DEVICE

(71) Applicant: EAKIN R&D LIMITED, Comber County Down (GB)

(72) Inventors: Benjamin Derek Mahood, Comber County Down (GB); Nathan Brennan, Comber County Down (GB); Sebastian Miller, Comber County Down (GB)

(73) Assignee: EAKIN R&D LIMITED, Comber County Dow (GB)

( * ) Notice: Subject to any disclaimer, the term of this patent is extended or adjusted under 35 U.S.C. 154(b) by 382 days.

(21) Appl. No.: 17/800,792

(22) PCT Filed: Feb. 22, 2021

(86) PCT No.: PCT/GB2021/050440
§ 371 (c)(1),
(2) Date: Aug. 18, 2022

(87) PCT Pub. No.: WO2021/165705
PCT Pub. Date: Aug. 26, 2021

(65) Prior Publication Data
US 2023/0081026 A1    Mar. 16, 2023

(30) Foreign Application Priority Data

Feb. 20, 2020    (GB) ..................................... 2002396

(51) Int. Cl.
*A61F 5/44*    (2006.01)
*A61F 5/443*    (2006.01)
*A61F 5/448*    (2006.01)

(52) U.S. Cl.
CPC ............ *A61F 5/4404* (2013.01); *A61F 5/443* (2013.01); *A61F 5/448* (2013.01)

(58) Field of Classification Search
CPC .......... A61F 5/44; A61F 5/445; A61F 5/4404; A61F 5/4405; A61F 5/4407; A61F 5/4408; A61F 5/448
See application file for complete search history.

(56) References Cited

U.S. PATENT DOCUMENTS 3,570,490 A    3/1971    Berger
4,519,797 A    5/1985    Hall
(Continued)

FOREIGN PATENT DOCUMENTS

EP        1400222 B1      1/2007
WO     2006026995 A1      3/2006

*Primary Examiner* — Susan S Su
*Assistant Examiner* — Erin A Kim
(74) *Attorney, Agent, or Firm* — Dinsmore & Shohl LLP

(57) ABSTRACT

An ostomy pouch or wound bag includes a fluid tight collecting bag for containing bodily fluid or waste matter. The collecting bag includes an opening for receiving bodily fluid or waste matter. A flexible material cover is provided that at least partially covers the collecting bag. The cover comprises a front part arranged on a first side of the collecting bag that in use faces forward away from the wearer. The front part of the cover includes a first panel section having a viewing window through which the opening is visible and a cover panel section that is reconfigurable between a closed configuration in which at least part of the cover panel section covers and obscures the viewing window and the opening is obscured, and an open configuration in which the viewing window is uncovered and the stoma opening is at least partially visible.

20 Claims, 9 Drawing Sheets

(56) References Cited

U.S. PATENT DOCUMENTS

| | | | |
|---|---|---|---|
| 2004/0059306 A1* | 3/2004 | Tsal | A61F 5/4404 604/332 |
| 2008/0300556 A1 | 12/2008 | Fenton | |
| 2018/0333290 A1* | 11/2018 | Jones | A61F 5/443 |

* cited by examiner

COLLECTING DEVICE

CROSS-REFERENCE TO RELATED APPLICATIONS

This application is the U.S. National Stage of PCT/GB2021/050440 filed on Feb. 22, 2021, which claims priority to United Kingdom Patent Application 2002396.6 filed on Feb. 20, 2020, the entire content of both are incorporated herein by reference in their entirety.

FIELD OF THE INVENTION

The present invention relates to a collecting device such as an ostomy pouch or wound bag, and in particular an ostomy pouch with a viewing window configured to enable stoma inspection and flange alignment.

BACKGROUND OF THE INVENTION

Ostomy procedures such as colostomy, ileostomy and/or urostomy, result in a portion of the patient's ileum or colon protruding through an opening in the patient's abdomen. The protruding end section of the ileum or colon is referred to as a stoma. Following an ostomy procedure, a collection device is required for collecting waste from the patient's stoma, which may be urine or faeces depending on the ostomy procedure and the nature of the stoma. Typically, a collection bag or 'ostomy pouch' is provided that receives the stoma and collects the waste.

Ostomy pouches consist generally of two sheets of flexible impermeable plastic film that form front and rear walls that are welded together around their periphery to form a common edge seal. The pouch will include an inlet for receiving the stoma and will typically also be provided with a drainage system to enable the pouch to be periodically emptied by the patient as it fills.

A mounting plate is provided for mechanically securing the ostomy pouch to the body of the wearer. In a one-piece ostomy system, the mounting plate is secured to the pouch and has an aperture that defines the inlet opening of the pouch. The mounting plate has an adhesive rear surface that secures the mounting plate and the pouch to the wearer's body. In a two-piece system the mounting plate is separate to the pouch and is secured to the wearer independently. An annular coupling arrangement is provided around the inlet opening of the pouch, and a corresponding coupling arrangement is provided on the mounting plate that allows the pouch to be releasably secured to the mounting plate. The user is therefore able to detach and replace the pouch without having to remove and change the mounting plate.

The plastic film forming the pouch is typically transparent, such that the contents of the pouch are visible through the film walls. It is generally undesirable for the contents of the pouch to be visible during normal use. In addition, the plastic film of the pouch can be uncomfortable if held in direct contact with the wearer's skin. In order to preserve wearer dignity and improve comfort it is known to provide pouch covers, typically formed from a fabric material, to obscure the contents of the plastic pouch and provide a barrier or 'comfort' layer between the pouch and the wearer's skin. However, visibility of the stoma and/or the contents of the pouch may be periodically required by a care giver, for example to check the condition of the stoma or to observe stoma output. It is also preferable to be able to view the stoma inlet when applying the stoma baseplate around the stoma, to ensure accurate alignment and minimise gaps to reduce leakage or skin irritation that may result from poor fitting.

Pouch covers are therefore commonly provided with a slit or opening on the opposing side of the bag to the inlet, that allows the fabric of the pouch to be manually parted and held open to provide visual access to the pouch. The viewing slit is typically created by forming the front wall of the pouch, that is to say the wall of the pouch that faces outwardly away from the wearer in use, from a lower panel and an upper panel. The lower panel extends to a height just above the stoma inlet and is sealed to the rear wall about its peripheral edge. The upper panel extends from the upper end of the pouch to a position proximate the stoma inlet. The lowermost edge of the upper panel extends downward past the upper end of the lower panel, such that the upper panel partially overlaps and sits over the upper end of the lower panel. To view the stoma the lower edge of the upper panel is lifted. The uncovered upper edge of the lower panel continues to obscure the stoma inlet at this stage. The upper edge of the lower panel is then gripped and pulled downwards, thereby creating an opening and exposing the stoma for inspection. When the upper and lower panels are released the opening closes and the stoma inlet is once again obscured from view.

Wound bags are provided for managing fistulae, multiple or irregular stomas, and high output wounds. A wound bag typically comprises a transparent collecting bag having an opening for receiving bodily fluid and a seal that surrounds the opening and secures to the wearer's body. Similar to an ostomy pouch, comfort covers may be provided and it becomes necessary for the care giver or wearer to be able to view the wound site through the cover. It is also known to provide wound bag covers having a slit arrangement for viewing the wound site similar to the arrangements described above.

The above process requires the care giver to manually open the viewing slit every time inspection is required. Where frequent monitoring of the stoma and/or the pouch contents is necessary, the requirement to manually open the viewing slit is inconvenient, particularly when several patients are being monitored by the same care giver. In addition, the requirement to use both hands to open the viewing slit prevents the care giver from being able to perform other tasks while viewing the stoma and hinders application of the stoma baseplate when fitting the pouch.

It is therefore desirable to provide an improved collecting device such as an ostomy pouch or wound bag which addresses the above described problems and/or which offers improvements generally.

SUMMARY OF THE INVENTION

According to the present invention there is provided an ostomy pouch as described herein.

In an embodiment of the invention there is provided a collecting device such as an ostomy pouch or wound bag comprising a fluid tight collecting bag for containing bodily fluid or waste matter. The collecting bag includes an opening for receiving bodily fluid or waste matter. A flexible material cover is provided that at least partially covers the collecting bag. The cover comprises a front part arranged on a first side of the collecting bag that in use faces forward away from the wearer. The front part of the cover includes a first panel section having a viewing window through which the opening is visible and a second panel section that is reconfigurable between a closed configuration in which at least part of the second panel section covers the viewing window and the opening is obscured, and an open configuration in which the viewing window is uncovered and the stoma opening is at least partially visible.

The cover preferably also includes a rear part on the opposing side of the collecting bag to the front part that in use is located between the collecting bag and the wearer to provide a comfort layer between the collecting bag and the wearer.

The viewing window and the arrangement and configuration of the second panel enables the stoma opening to be revealed in a single operation by lifting the second panel section. In contrast, the slit openings of the prior art require the upper and lower sections of the front panel to be moved to reveal the stoma opening. If the upper or lower section is moved on its own, the other section continues to cover and obscure the stoma opening. Furthermore, even when two hands are used it is difficult to sufficiently uncover the stoma opening to achieve a full and satisfactory view.

The collecting device is preferably an ostomy pouch and the opening is a stoma opening for receiving a stoma.

The cover is formed from an opaque material and at least the front wall of the collecting bag is formed of a transparent material.

The collecting bag preferably comprises a front wall and rear wall, and at least the front wall is transparent. The front and rear walls are also preferably formed of a flexible polymeric film material. At least the front part of the cover and the front and rear walls of the collecting bag cover are bonded together along their peripheral edges to form a laminated seam. Preferably the rear part of the cover is also bonded to the front part of the cover and the front and rear walls of the collecting bag as part of the laminated seam, although in other embodiments the cover may include only a front part.

Preferably the layers are welded together. However, the term "bonded" means any form of securing the layers together by means of adhesive, heat, pressure or by chemical bonds, which may comprise welding such as thermal or RF welding, adhesives, or by any other suitable means.

The pouch may further comprise a mounting plate, also referred to as a mounting flange, having an adhesive rear surface for securing the mounting plate to the skin of a wearer, and an aperture for receiving the stoma that is aligned with the stoma opening of the collecting bag. An expansion region surrounds the aperture of the mounting plate, and the aperture of the mounting plate may be enlarged within the expansion region by cutting the mounting plate. The viewing window is configured such that the stoma opening, and the expansion region are visible therethrough. Visible means at least partially visible. The viewing window is thereby able to display the stoma opening even when it is expanded to its maximum diameter. In a one-piece ostomy system, the mounting plate may have a front surface bonded to the rear wall of the collecting bag in a bonding region, and the stoma opening and bonding region are visible through the window. Preferably the bonding region is larger than the expansion region. As the collecting bag is bonded to the mounting plate the inlet aperture of the mounting plate defines the stoma opening.

At least part of the outer peripheral edge of the second panel may be bonded to the collecting bag and the second panel includes a flap portion that is movable between the open and closed configurations. The outer peripheral edge is the edge that is coincident and aligned with the outer edge of the collecting bag. The flap may be folded, rolled or otherwise moved to the open configuration.

The first panel section has an upper edge that extends laterally across the collecting bag and the upper edge is shaped to form the viewing window. At least part of the upper edge is located below the opening to expose the opening when the upper panel section is in the open position. Preferably the upper edge comprises a curved cut away section that forms the viewing window. The upper edge may have outer parts that are located level with or above the stoma opening at a first height and the base of the curved cut away section is located at a second height that is lower than the first height and lower than the height of the stoma opening. Preferably the second height corresponds to the base of the bonding region.

The curved cut away section preferably has a concave substantially semi-circular shape to enable it to follow the shape of the bonding region. Semi-circular means substantially semi-circular, that is to say an arcuate shape that approximates a semi-circle but which may span more or less than 180 degrees. Alternatively, the cut away section may have any shape suitable for revealing the stoma opening and to be covered by the overlying second panel section. The cut away may for example be v-shaped, u-shaped, square or rectangular.

The expansion region of the mounting plate is substantially circular and concentric with the stoma opening and the substantially semi-circular cut away section.

The bonding region between the mounting plate and the collecting bag is substantially circular and concentric with the stoma opening, and the substantially semi-circular cut away section has a radius corresponding to the radius of the bonding region, such that at least part of the semi-circular edge of the cut away is aligned with the outer edge of the bonding region.

The first panel section is preferably bonded to the collecting bag around its outer peripheral edge defining a lower bonding seam, and the second panel section is bonded to the collecting bag around its outer peripheral edge defining an upper bonding seam, and the upper ends of the lower bonding seam and the lower ends of the upper bonding seam are immediately adjacent each other such that the outer bonding seam between the front part and the collecting bag is effectively continuous.

The lower ends of the upper bonding seam define the outer ends of a fold line about which the flap portion of the second panel is foldable to move between the open and closed configurations. As the second panel is fixed to the collecting bag by the bonding seam, and the lower edges of the bonding seam are lowest parts at which the second panel section is fixed, the free part of the second panel below these points is able to move and fold, with the lower ends defining the limit of free movement and hence forming the fold line.

In the closed configuration the flap portion of the second panel preferably extends downwardly below the fold line and at least partially overlaps the fixed panel. The lower edge of the second panel preferably sits outside the upper edge of the lower panel section such that the upper panel section completely covers the upper edge of the lower panel section.

The flap portion preferably tapers inwardly in the downward direction in the closed configuration, minimising the size of the flap while ensuring the window is fully covered. The fold line is preferably spaced above the stoma opening, such that when the flap is folded upwardly the fold is located above the stoma opening ensuring the stoma is fully revealed.

Secondary holding means may be provided for holding the flap in the closed configuration. The secondary holding means may comprise a first fastener secured to the inner side of the flap and a second fastener secured to the lower panel section or the collecting bag. The secondary holding means may be one of a hook and eye fastener secured to the inner surface of the flap and the other of the hook and eye secured to the lower panel section. Alternatively, the secondary holding means may comprise a button or buttons, poppers, adhesive or any other suitable fastening means.

The cutaway section of the fixed panel curves convexly downwards away from the fold line.

Holding means are preferably provided that are arranged to hold the second panel section in the open configuration. The holding means may be any suitable fastener, connector or other retaining device that maintains the second or upper panel section in the open configuration.

The holding means is preferably configured to fix the flap section of the second panel section in a raised position corresponding to the open configuration.

Preferably the holding means comprises a retaining slit located at the lower end of the flap portion and a locking tab projecting from the upper end of the pouch and the retaining slit and the locking tab are configured and arranged such that the locking tab is able to be inserted through the slit when the flap portion is in the open configuration to hold the flap portion in the open configuration. This arrangement enables the lower end of the flap portion to be easily hooked over the locking tab at the upper end of the pouch to hold the flap in the open configuration. Alternatively, the holding means may comprise Velcro, poppers, buttons, non-permanent adhesive or any other suitable fastening means. In another embodiment the holding means may comprises a reinforced zone on the flap that stiffens the flap and allows it to remain upright in the open configuration without the requirement for a fastener or coupling.

Preferably the second panel section comprises at least one fabric layer and at least one polymer film layer, the second panel section has a lower edge and strengthening zone is formed along or adjacent at least part of the lower edge that is formed by a region of bonding between the at least one fabric layer and at least one polymer film layer.

Preferably the retaining slit is formed within the strengthening zone at the lower edge of the second panel section.

The second panel section may include a flap portion having an inner side that faces towards the collecting bag in the closed configuration and a first fastener is located at the lower end of the rear part of the cover and a corresponding second fastener is located on the inner side of the flap, and the pouch is foldable to a compact configuration in which the lower end of the rear part is folded upwardly and located beneath the flap portion of the front part. The first and second fasteners are configured to cooperate to hold the pouch in the compact configuration. The first fastener may be secured to the rear fabric panel or directly to the rear wall of the collecting bag—in the latter arrangement the rear fabric panel includes an aperture surrounding and exposing the fastener. The second fastener may be secured to a rear fabric layer of the flap or to an intermediate polymer film layer.

In another aspect of the invention there is provided a collecting device such as an ostomy pouch or wound bag comprising a fluid tight collecting bag for containing bodily fluid or waste matter. The collecting device is configured to be worn on a person with an inner side that faces the wearer in use and an outer side that face away from the wearer. The collecting bag includes an opening for receiving bodily fluid or waste matter. A flexible material cover is provided that at least partially covers the collecting bag. The cover comprises a front part arranged on a first side of the collecting bag that in use faces forward away from the wearer. The front part of the cover includes upper panel section at least part of which defines a movable flap having an inner side facing the collecting bag and an outer side, and wherein the device is reconfigurable between an expanded configuration and compact configuration in which a lower part of the device is folded upwardly and retained beneath the flap.

A first fastener is preferably located on an inner side of the flap and a second fastener is located on the rear side of the device, the first and second fasteners being configured to align in the compact configuration and cooperate to hold the pouch in the compact configuration. The second fastener is preferably located at the lower end of the device on the rear side. The first and second fasteners may be hook and eye fasteners such as Velcro®. Alternatively, the first and second fasteners may comprise a slit and a corresponding locking tab which interlink to hold the device in the compact configuration.

The second fastener may be bonded to the rear wall of the collecting bag and the rear part of the cover may include an aperture that surrounds and reveals the second fastener. The rear part of the cover may be bonded to the rear wall of the collecting bag in a region surround the aperture.

In another aspect of the invention there is provide a collecting device such as an ostomy pouch or wound bag comprising a fluid tight collecting bag for containing bodily fluid or waste matter. The collecting bag includes an opening for receiving bodily fluid or waste matter. A flexible material cover is provided that at least partially covers the collecting bag. The cover comprises a front part arranged on a first side of the collecting bag that in use faces forward away from the wearer. The front part of the cover includes an upper panel section and a lower panel section. The upper panel section includes a flap portion having an inner side that faces towards the collecting bag in a closed configuration and wherein a first fastener is located at the lower end of the rear part of the cover and a corresponding second fastener is located on the inner side of the flap, and the pouch is foldable to a compact configuration in which the lower end of the rear part is located beneath the flap portion of the upper panel section and the first and second fasteners are configured to cooperate to hold the pouch in the compact configuration. This embodiment may be practiced with or without a viewing window located beneath the flap.

BRIEF DESCRIPTION OF THE DRAWINGS

The present invention will now be described by way of example only with reference to the following illustrative figures in which.

DESCRIPTION OF THE PREFERRED EMBODIMENTS

Figure 1:
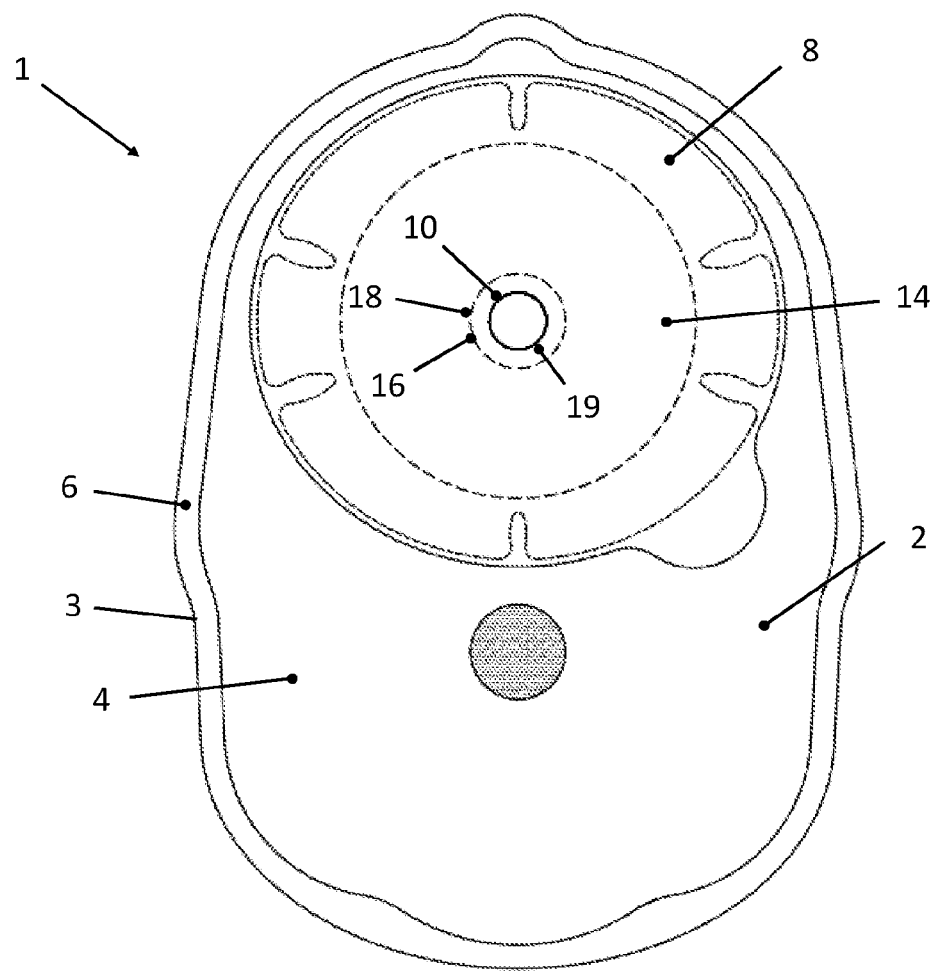
FIG. 1 is a rear view of an ostomy pouch according to an embodiment of the present invention.

Referring to FIG. 1, there is provided an ostomy pouch 1 including a sealed waterproof collecting bag 2 formed from two opposing films of flexible impermeable material. The collecting bag 2 is preferably formed from a plastics film material known in the art for forming ostomy pouches and may be a multiple ply film, although it will be appreciated that other suitable materials could be used. The two opposing films define a front wall 3 and a rear wall 4. The front wall 3 and rear wall 4 are sealed along their common peripheral edges 6 to form a receptacle for receiving liquid and solid waste. The peripheral edges 6 may be sealed by welding such as thermal or RF welding, bonded such as by adhesion, or by any other suitable means.

A mounting plate or flange 8 is provided for mechanically securing the ostomy pouch 1 to the body of the wearer. The present embodiment relates to a one-piece ostomy system in which the mounting plate 8 is secured to the rear wall 4 of the collecting bag 2. It will however be appreciated that the invention is also applicable to a two-piece ostomy system in which the mounting plate is releasably connectable to the collecting bag by a coupling arrangement. The mounting plate 8 is an adhesive wafer comprising a foam disc and a hydrocolloid skin barrier layer, which are adhered together to form a flexible adhesive pad. The mounting plate 8 may be a flat disc or may include a convex central portion. Where the mounting plate 8 includes a convex central portion, it may further include a plastic mounting plate which provides a stiffer substrate to which the foam and hydrocolloid layers conform, enabling the convex profile to be maintained.

The rear wall 4 of the collecting bag 2 is sealed to the front face of the mounting plate 8 at a bonding region 14. The term 'front' as used herein refers to a surface which in use faces away from the body of the user, and the term 'rear' refers to a surface which in use faces towards the body of the wearer. The terms 'upper', 'lower', 'top' and 'bottom' as used herein relate to the pouch as oriented on the wearer in use. The mounting plate 8 includes an aperture 10 arranged substantially centrally on the mounting plate 8. The bonding region 14 is annular and surrounds the aperture 10. A corresponding aperture 16 is formed in the rear wall 4 with an edge 18 to which the inner edge of the sealing region 14 extends such that the rear wall 4 is sealed to the mounting plate 8 around the entire periphery of the aperture 16. A region 19 of the mounting plate 8 extends radially inwards from the inner edge 18 of the aperture 16 to the edge of the aperture 10.

The aperture 16 defines an inlet opening into the collecting bag 2 through which the wearer's stoma is extended in use. The mounting plate 8 surrounds the stoma in use. The size of the stoma inlet 10 formed in the mounting plate 8 is able to be selectively increased within an expansion zone defined on the mounting plate 8 by cutting the mounting plate 8, and guide-lines may be printed on the mounting plate for indicating openings of increasing diameter to assist in accurate cutting of the stoma inlet 10. The bonding layer 14 is sized to be larger than the expansion zone, the outer boundary of which defines the maximum stoma inlet size, so there is always of region of bonding between the bag 2 and the mounting plate 8 that surrounds and seals the stoma opening 10. The hydrocolloid adhesive layer at the rear surface of the mounting plate 8 provides a barrier seal with the wearer's skin extending from the peripheral edge 18 of the mounting plate 8 to the stoma inlet 10. In this way, when the stoma is extended through the stoma inlet 10 in use a barrier seal is created between the mounting plate 8 and the skin of the wearer that is airtight and watertight from the edge of the stoma inlet 10 outwardly, thereby sealing the contents of the collecting bag 2 from the external environment.

The mounting plate 8 is arranged at the upper end of the pouch 1 such that when the pouch 1 is arranged vertically in use a significant portion of the volume of the collecting bag 2 is arranged beneath the opening 10. In use, waste from the stoma passes directly into the volume of the collecting bag 2 beneath the stoma inlet 10.

Figure 2:
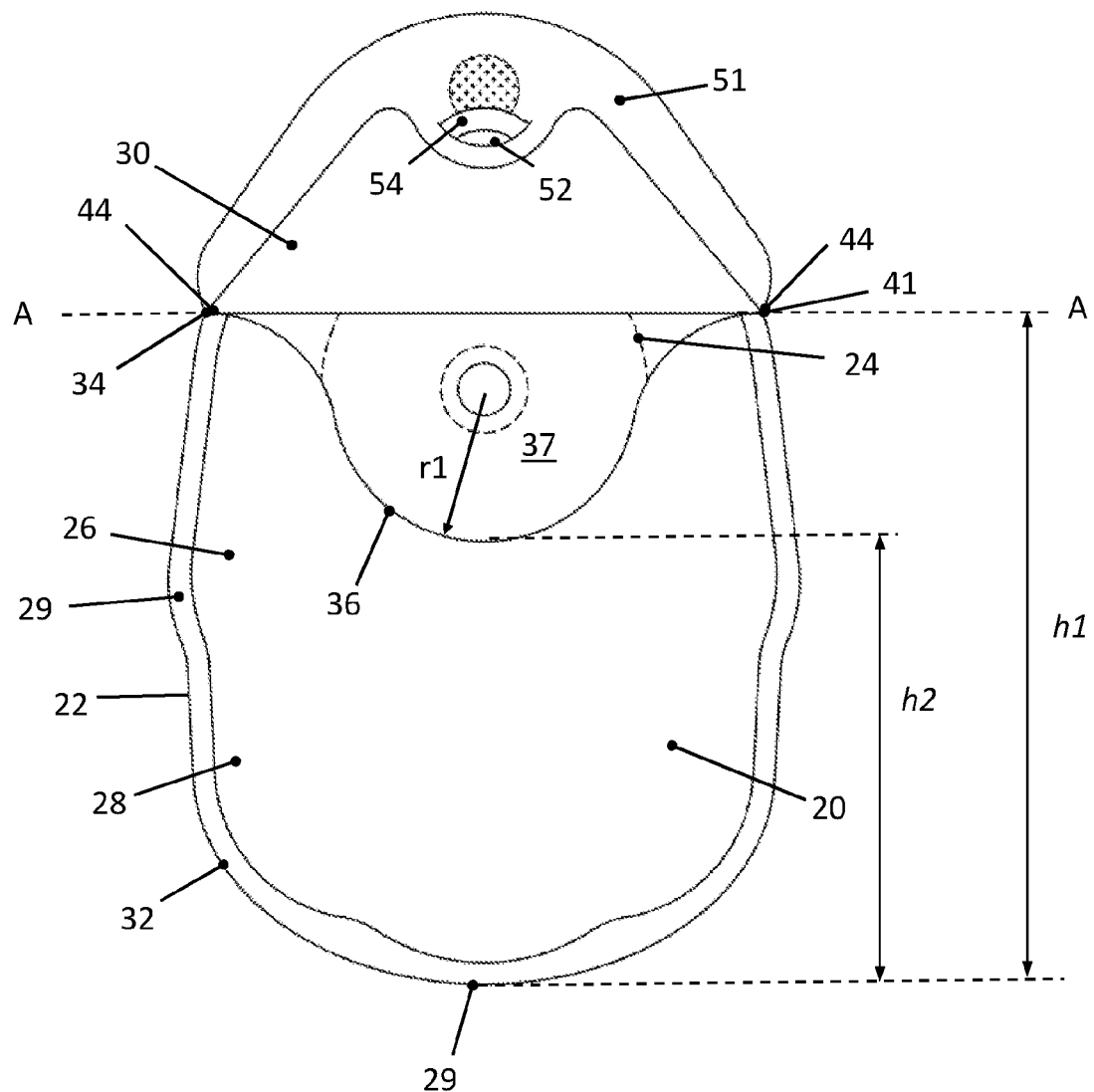
FIG. 2 is a front view of the ostomy pouch of FIG. 1 with the flap in the open configuration.

As shown in FIG. 2, the pouch 1 includes a cover 20 for covering the collecting bag 2. The cover 20 is formed from an opaque, lightweight comfort fabric, that may be a woven or a non-woven material that is bio-sensitive to avoid skin irritation. The cover material may for example be formed from polyethylene, polypropylene or polyester fibres. The cover 20 includes a rear panel 22 arranged at the outer surface of the rear wall 4 such that in use it is located between the rear wall 4 and the wearer's skin. The rear panel 22 has a shape conforming to the shape of the collecting bag 2 with the peripheral edge of the rear panel 22 and the peripheral edge of the rear wall 4 being aligned. The rear panel 22 is located between the rear wall 4 and the mounting plate 8. Therefore, the rear panel 22 is provide with an aperture 24 corresponding in size and shape to the outer edge of the bonding region 14 between the rear wall 4 and the mounting plate 8. In this way, mounting plate 8 is able to bond to the rear wall 4 in the bonding region 14 of the rear wall 4 exposed by the aperture 24. The rear panel 22 is bonded to the rear wall 4 of the collecting bag 2 along its peripheral edge by RF or thermal welding, wherein rear wall 4 is caused to melt and partially penetrate the material of the rear panel 22 to bond the rear panel 22 to the rear wall 4. The welding process is controlled such that the plastic material of the rear wall 4 does not penetrate to the outer surface of the rear panel 22, such that the comfort feel of the fabric material at the outer surface is maintained.

The cover 20 further includes a front section 26 comprising a lower panel 28 and an upper panel 30. The lower panel 28 has a peripheral edge 32 that conforms to the shape of the front wall 3. The outer peripheral edge of the lower panel 28 is bonded to the underlying peripheral edge of the front wall 3 by RF of thermal welding in the same manner as the rear panel 22 is bonded to the rear wall 4. The upper edge 34 of the lower panel 28 includes a cut away section 36 that is configured to reveal the underlying stoma inlet 10 and bonding region 14 of the mounting plate 8. At the outer edges of lower panel 28 the upper edge 34 extends to a height h1 from the base 29 of the pouch 1. Inboard of the outer edges, the upper edge 34 curves downwardly to form a scalloped, substantially semi-circular cut away having a radius r1 corresponding to the radius of the bonding region 14, and a lowermost point at height h2. The cut away section 36 is aligned with the bonding region 14, with the cut away section 36 defining a viewing window 37 configured such that the bonding region 14 and the stoma inlet 10 are substantially uncovered by the lower panel 28. The bonding region 14 will always be larger than the stoma inlet 10, and therefore ensuring the bonding region 14 is fully visible through the viewing window means the stoma inlet 10 will always be fully visible.

Figure 3:
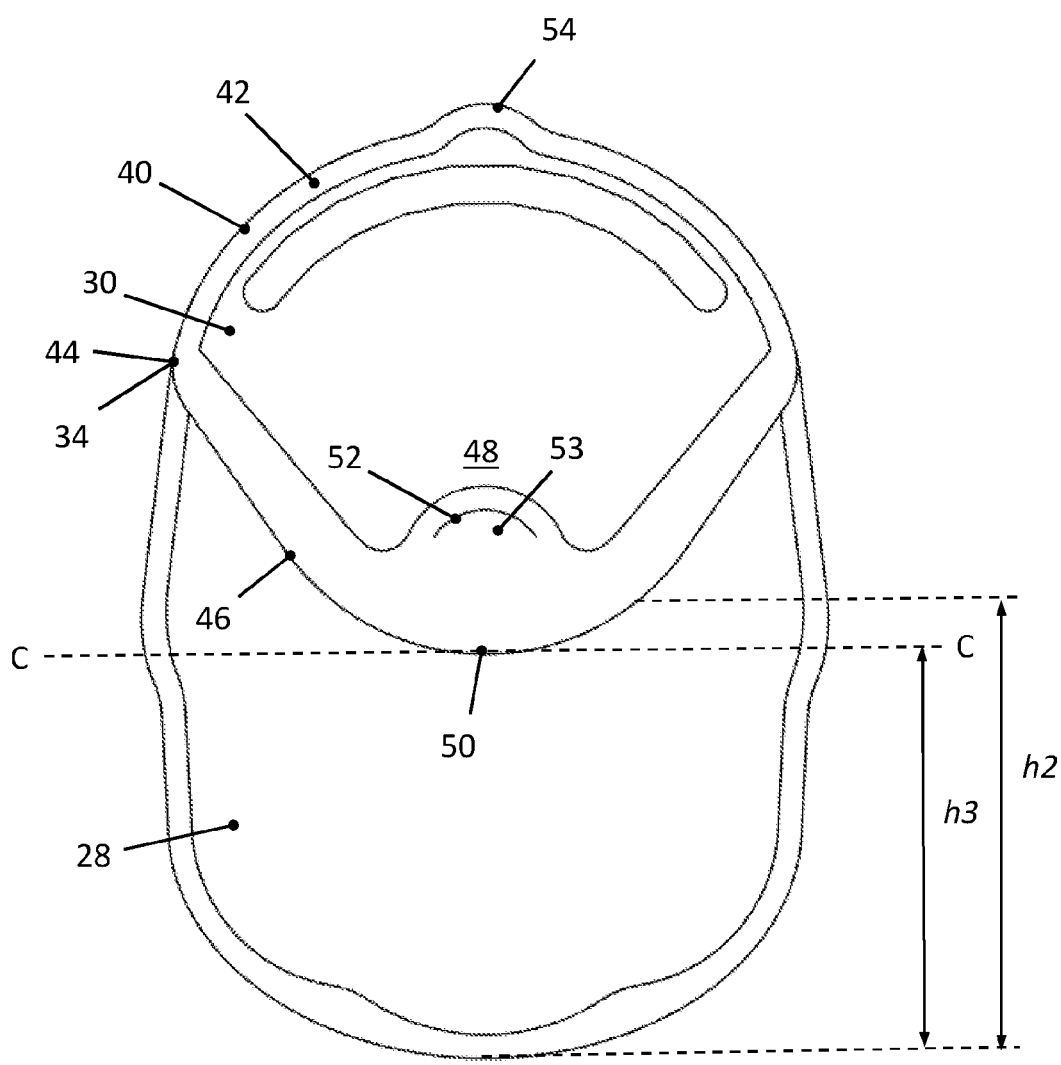
FIG. 3 is a front view of the ostomy pouch of FIG. 1 with the flap in the closed configuration.

FIG. 3 shows the closure flap 48 in the closed configuration. The upper panel 30 is arranged above the lower panel 28 and forms a flap for covering the viewing window 36 of the lower panel 28. In the closed configuration the upper panel 30 covers the viewing window 37 of the lower panel 28 and obscures the underlying mounting plate 8 and stoma inlet 10 from view. The upper panel 30 has an outer peripheral edge 40 that corresponds to the shape of the underlying front wall 3. The outer peripheral edge 40 of the upper panel 30 is bonded to the underlying peripheral edge of the front wall 3 by RF or thermal welding in the same manner as the rear panel 22 is bonded to the rear wall 4. The lower ends 44 of the peripheral bonding seam 42 are adjacent to the upper edge 34 of the lower panel 28 at height h1. The lower edge 46 of the upper panel 30 is free and is not bonded to the front wall 3. The lower edge 46 tapers downwardly an inwardly from either side to form a substantially v-shaped flap 48. The lower end 50 of the flap 48 is located at height h3, lower than height h2, and has a curved form corresponding to, and spaced radially outwardly of and beneath the curved edge of the cutaway section 36. The flap 48 extends downwardly past the upper edge 34 of the lower panel and overlaps the lower panel 28 to obscure the viewing window 37.

The upper panel 30 is formed of two fabrics layers and an intermediate polymer film layer that may be the same film material as the collecting bag 2. The three layers are bonded together about their peripheral edges by RF or thermal welding as described above, such the intermediate layer melts and penetrates both fabric layers. The triple ply thickness of the upper panel 30 provides additional weight that helps maintain the flap 48 in the closed configuration. The lower edge 46 of the upper panel 30 is provided with a bonding region 51 of increased thickness between the two layers of the upper panel 28 as measured inwardly from lower edge 46. The thickened bonding region 51 increases stiffness along the lower edge 46, which maintains the form of the flap 48 and further assists in maintaining the flap 48 in the closed configuration, for example by preventing wrinkling of the flap 48. A curved slit 52 is formed in the bonding region 51, inboard of the tip 50 of the flap 48 at the centre of the flap 48. The slit 52 curves upwardly, in a convex manner away from and in the opposing direction to the downward curve of the tip. A locking tab 54 projects from the upper end of the cover 20 at its apex and is laterally aligned with the slit 52. The slit 52 and locking tab 54 are used to hold the flap in the open configuration, as will be described in further detail below. In an alternative arrangement, the slit 52 may be configured such that it receives and hooks over the curved upper edge 40 of the upper panel section 30 such that a portion of the curved upper edge 40 defines the locking tab without the requirement for a pronounced projection.

Referring again to FIG. 2, the lower ends 44 of the bonding region 42 are the lowest points at which the upper panel 20 is secured to the front wall 3. The lower end 44 of the bonding region 42 locate immediately adjacent the upper ends 41 of the peripheral bonding region 29 of the lower panel 28. The point at which the lower ends 44 of the bonding region 42 and the upper ends 41 of the bonding region 29 meet defines the outer edges of a fold line A-A about which the flap 48 is folded upwards. The height h1 at which the lower ends 4 are located, and hence the height of the fold line A-A is above the height of the stoma inlet 10. As such, when the flap 48 is folded upwards the stoma opening 10 and the viewing window 36 are uncovered, allowing full visibility of the stoma inlet. The curved shape of the viewing window forms side parts 56 which cover the underlying collecting bag 2 and ensure that only the section of the collecting bag 2 within the viewing window 36 is visible, thereby limiting the extent to which the contents are exposed.

In the open configuration, the slit 52 in the flap 48 is hooked over the upwardly extending locking tab 54 such that the locking tab 54 extends through the slit 52. Hooking the slit 52 over the locking tab 54, the flap is held in the upwardly folded open configuration. The stiffened bonding region 51 maintains the form of the flap 48 when in the upwards open configuration and prevents the tip of the flap 48 from flopping downwards. In other embodiments alternative holding means may be provided. For example, the lower end of the flap 48 may be provided with a Velcro tab, and a corresponding Velcro tab may be affixed at the upper end of the flap 48 and positioned such that it is aligned with the lower Velcro tab when the flap 48 is folded to the open configuration to connect therewith.

In use, when a care giver wishes to inspect the wearer's stoma and/or monitor stoma output or the contents of the pouch the flap 48 is moved to the open configuration by gripping the tip 50 and lifting the flap 48 upwardly. The flap 48 folds about fold line A-A as it is lifted. The flap 48 is then hooked over the tab 54, and the tab 54 inserted into the slit 52 to hold the flap 48 in the open configuration. The care giver is then provided with a full view of the stoma area and can periodically glance at the pouch and monitor the stoma condition and/or pouch contents from a distance, with less frequent close inspections required. If the wearer requires privacy, the flap 48 may be easily lifted and released from the locking tab 54 and folded down to return it to the closed configuration.

Figure 4:
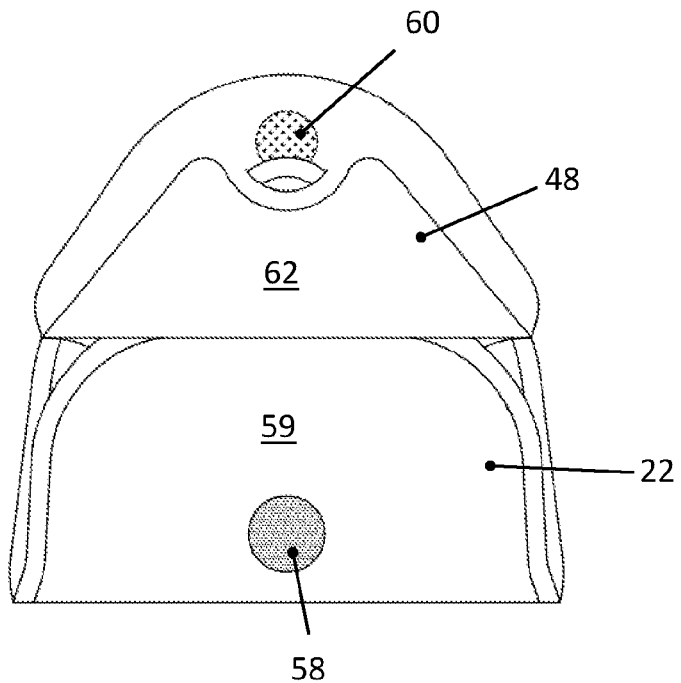
FIG. 4 is a front view of an ostomy pouch according to an embodiment of the present invention folded to the compact configuration with the flap raised.
Figure 5:
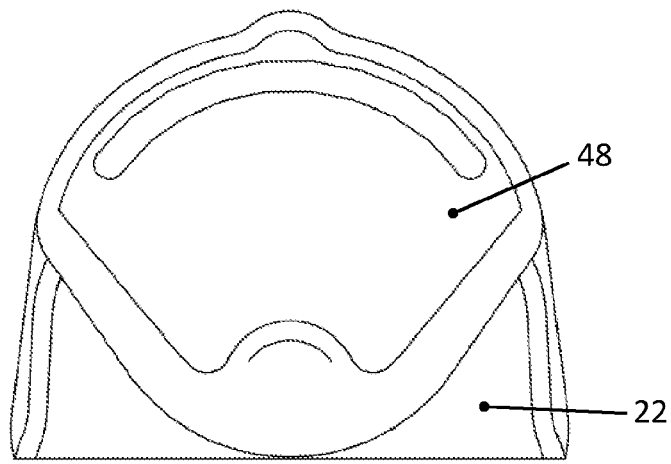
FIG. 5 is the ostomy pouch of FIG. 4 with the flap closed position.

Referring to FIG. 4, the pouch 1 is further provided with means for reducing the size of the pouch 1 if required, for example where output is low, and it is preferred to make the pouch 1 less noticeable. The rear panel 22 is provided with a fastener 58, for example a hook and eye fastener such as Velcro. The fastener 58 is affixed to the lower end of the rear panel 22 on its outer surface 59, although in alternative embodiments the fastener may be affixed directly to the rear wall 4 of the collecting bag 2. A corresponding fastener 60 is provided on the inner surface 62 of the flap 48, preferably towards the lower end 50 of the flap 48. It will be appreciated that the term 'lower' used herein is a relative term used with reference to the orientation of the flap 28 in the closed configuration. A fold line C-C is defined across the pouch 1 that is substantially aligned with the lower end 50 of the flap 48 at height h3. To reduce the size of the pouch the lower end of the pouch 1 is folded forwards and upwards such that the lower end of the rear wall 22 is now forward facing. The lower end of the pouch 1 is lifted upward and placed beneath the flap 48 until the fastener of the rear wall 22 and the fastener on the inner surface of the flap 48 are aligned. The fastener 58 and fastener 60 are located equidistant from the fold line C-C above and below the fold line C-C respectively such that when the lower end of the pouch is folded upwards about the fold line C-C the two fasteners 58,60 align. The two fasteners are secured to each other once in this position, and by doing so the pouch 1 is held in a folded, compact configuration in which it is substantially halved in length, as shown in FIG. 5.

Figure 6:
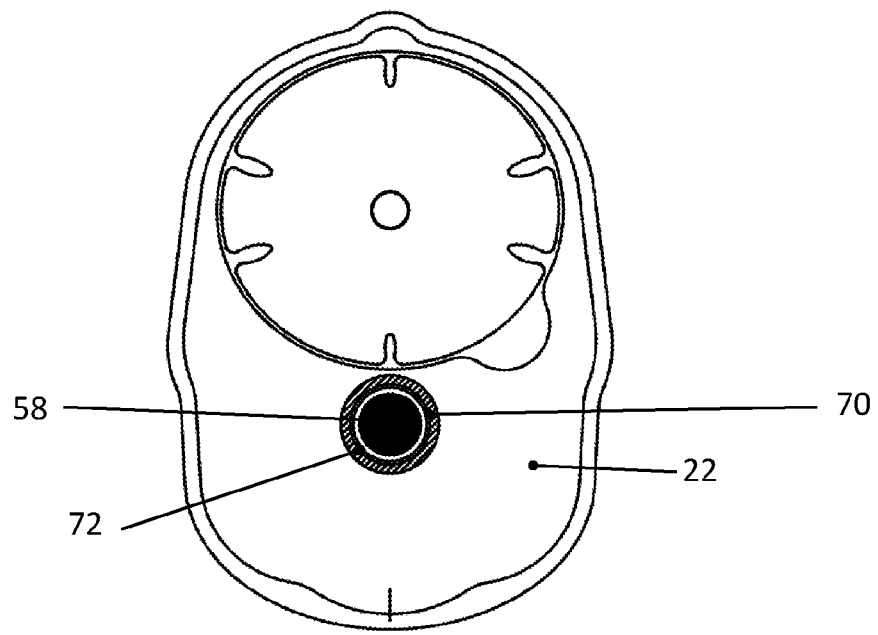
FIG. 6 is a rear view of an ostomy pouch according to another embodiment of the present invention.

In the arrangement of FIG. 6, an aperture 70 is formed in the rear panel 22 of the cover 20. The fastener 58 is affixed to rear wall 4 of the collecting bag 2 rather than to the rear panel 22. The aperture 70 corresponds in shape and location to the fastener 58 and is arranged about the fastener 58, with the fastener 58 being exposed through the aperture 70. This allows direct bonding of the fastener 58 to the polymer film of the rear wall 4 rather than to the fabric material of the cover 20. A more secure bond may be created with the polymer film of the rear wall 4 than with the fabric material, which mitigates the risk of the fastener 58 de-bonding in use. A strengthening zone 72 may be formed around the aperture 70 by a region of bonding between the rear panel 22 and the rear wall 4, in a similar manner to the strengthening zones described above. This ensures that the shape of the aperture is maintained and that the position of the aperture 70 is fixed relative to the fastener 59, ensuring the fastener 58 and aperture 70 remain aligned.

Figure 7:
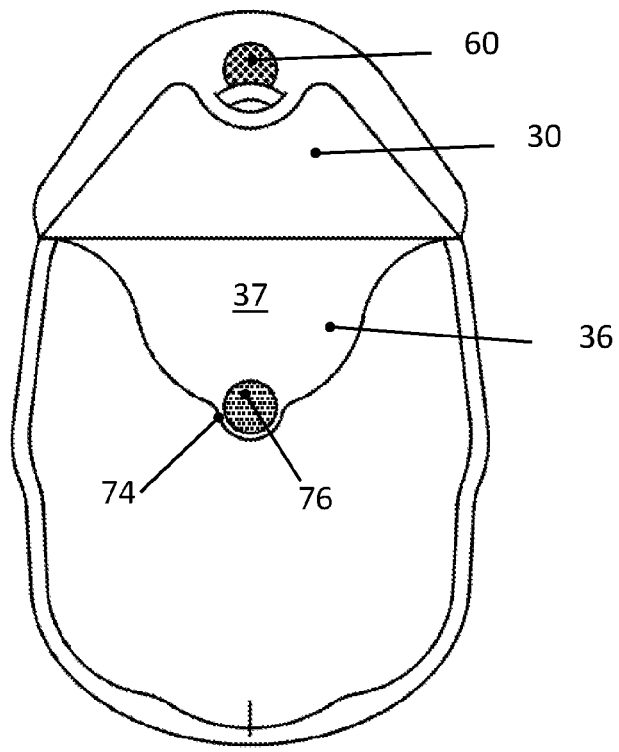
FIG. 7 is a front view of an ostomy pouch according to another embodiment of the present invention.

In the arrangement of FIG. 7 the cutaway section 36 of upper edge 34 of the lower panel 28 includes a secondary cutaway section or recess 74 located in the saddle of the cutaway 36. The substantially semi-circular recess 74 is arranged to reveal a fastener 76 bonded to the underlying front wall 3 of the collecting bag 2. The fastener 76 is a Velcro® tab or any other suitable fastener and is located at a level stoma inlet 10. The fastener 76 is arranged to align with the fastener 60 on the inside surface of the upper panel 30 to secure the upper panel section 30 to the front wall 3 and secure the upper panel section 30 in the closed position. The faster 76 and fastener 60 are corresponding complementary fasteners such as opposing parts of a hook and eye fastener such as Velcro®. Alternatively, they may be push fittings or any other suitable two-part fasteners. It will be appreciated that the semi-circular cutaway 74 is not essential and in other arrangements the fastener 76 may be bonded directly to the collecting bag 2 above the level of the first cutaway 36.

Figure 8:
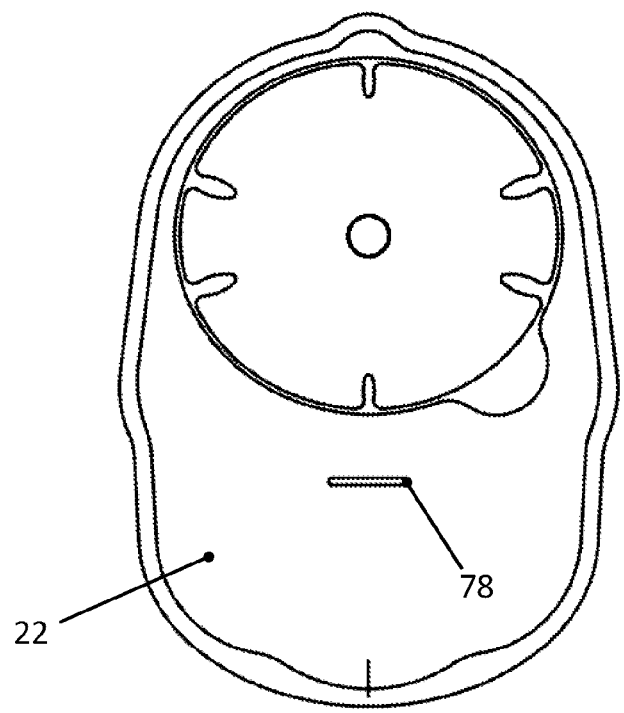
FIG. 8 is a rear view of an ostomy pouch according to another embodiment of the present invention.
Figure 9:
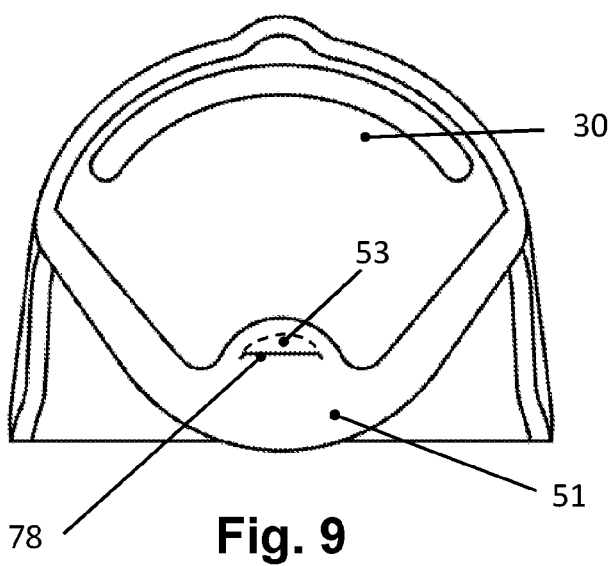
FIG. 9 is a rear view of the ostomy pouch of FIG. 8 in the compact folded configuration.

FIG. 8 shows an embodiment in which the fastener on the rear panel 22 comprises a transverse slit 78 formed in the material of the rear panel 22. The corresponding fastener of the upper panel section 30 is created by the curved slit 52 formed in the bonding region 51. The slit 52 forms a substantially semi-circular movable tab section 53, as can be seen in FIG. 3, that faces upwardly and folds about the lower ends of the slit 52. The slit 78 is arranged such that it is level with the tab 53 when the lower end of the pouch 1 is folded upwardly to the compact configuration. The lower end is tucked beneath the flap 48 and the tab 53 is bent rearwardly and inserted into the slit 78, extending upwardly into the slit 78. The lower end of the pouch 1 is thereby hooked over the tab 52 to hold the pouch 1 in the compact configuration, as shown in FIG. 9.

Figure 10:
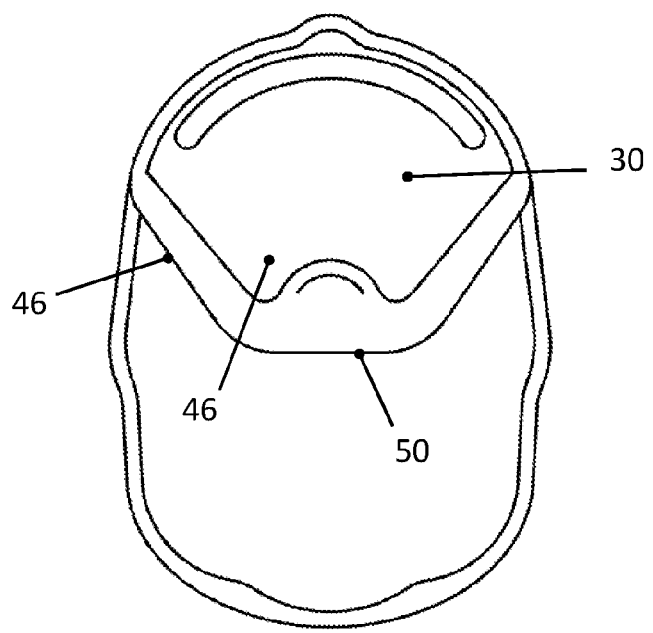
FIG. 10 is a rear view of an ostomy pouch according to another embodiment of the present invention.
Figure 11:
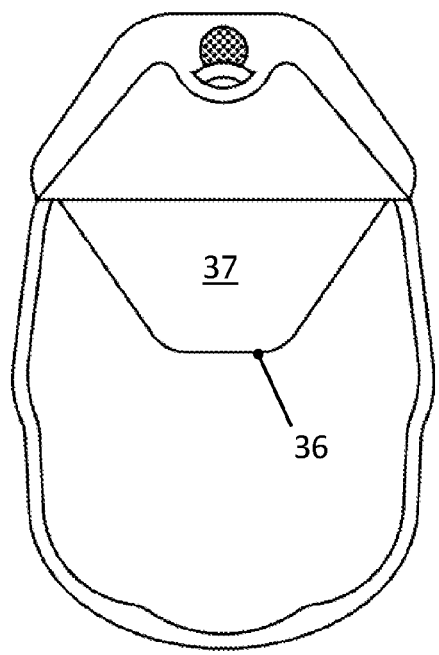
FIG. 11 is a front view of the ostomy pouch of FIG. 10.

In the alternative embodiment of FIG. 10, the lower edge 46 tapers downwardly and inwardly from either side to the lower end 50 of the flap 48, which is squared off rather than V-shaped such that it has a flat lower edge. The cutaway section 36 defining the window 37 is provided with a corresponding squared off shape, as shown in FIG. 11.

Figure 12:
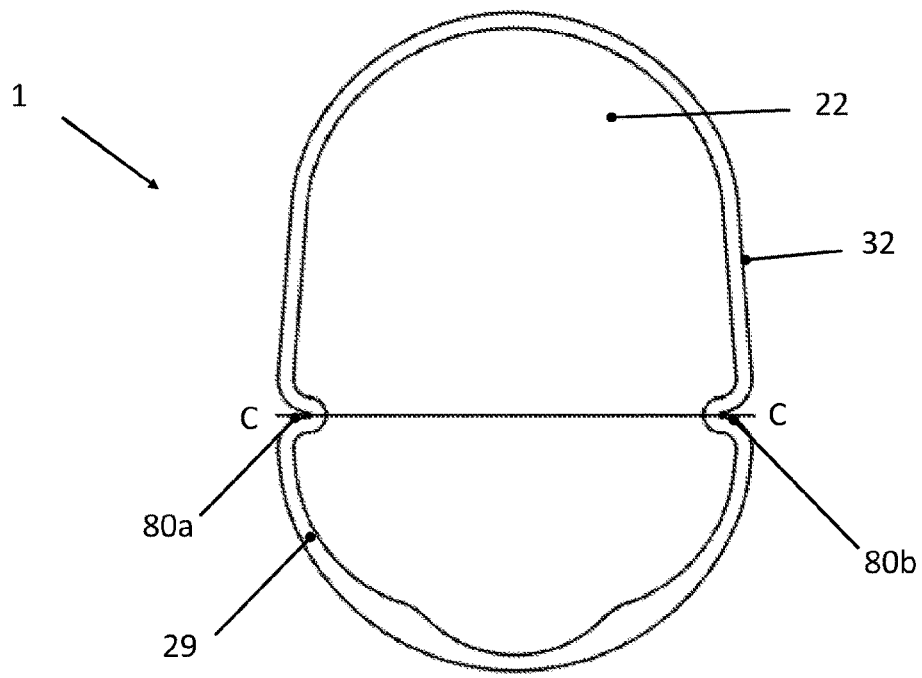
FIG. 12 is a rear view of an ostomy pouch according to another embodiment of the present invention.
Figure 13:
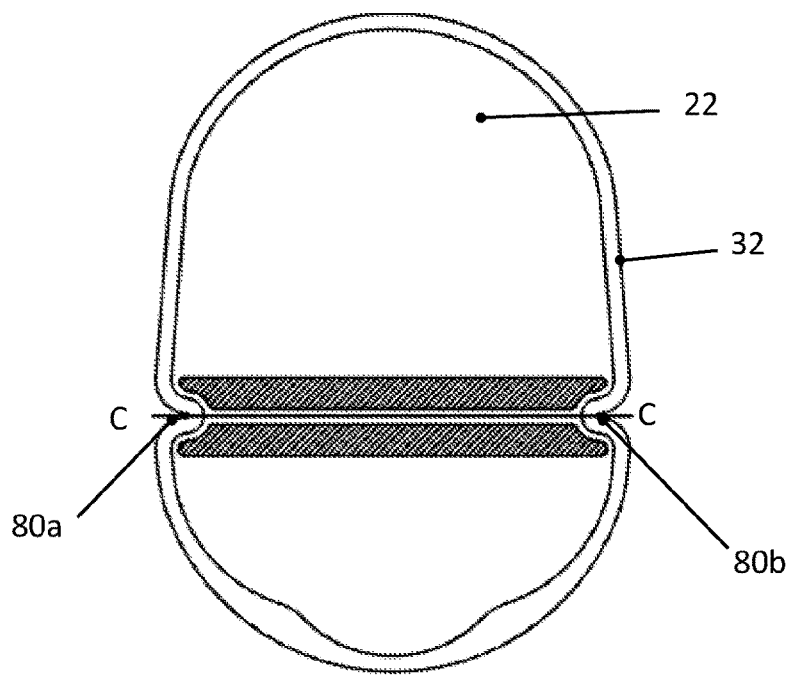
FIG. 13 is a front view of the ostomy pouch of FIG. 12.

In the arrangement of FIG. 12, the peripheral edge 32 of the lower end of the pouch 1 includes notches or slits 80a and 80b formed by the peripheral edge curving inwardly to create a valley. The notches or slits 80a and 80b are arranged on opposing sides of the pouch 1 at a common height h3 corresponding to the fold line C-C. The peripheral weld 29 follows and confirms to shape of the notches 80a and 80b, which creates a hinge point in the peripheral edge 32 at the fold line C-C as well as providing a visual indication of the fold line C-C. This improves the ease of folding the pouch 1 and ensures more accurate and immediate alignment of the fasteners 58,60.

Figure 14:
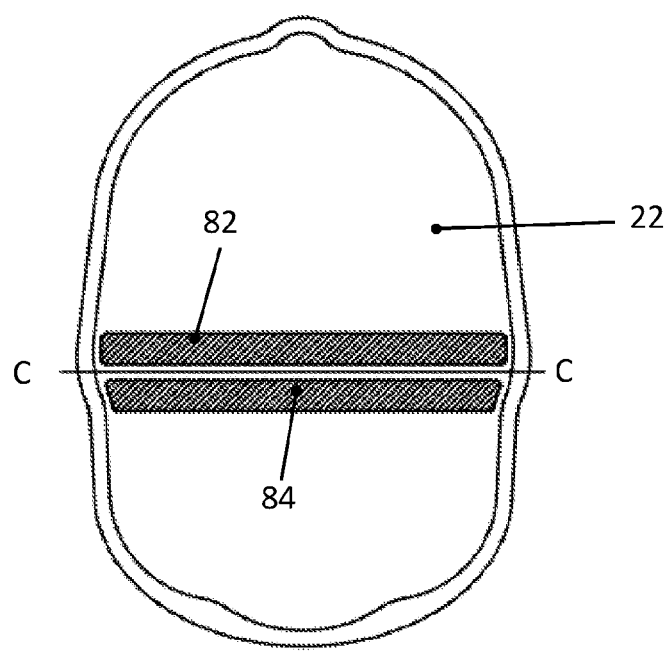
FIG. 14 is a rear view of an ostomy pouch according to a yet further embodiment of the present invention.

Folding of the pouch 1 about the fold line C-C is further enhanced by lateral stiffening elements 82 and 84 located on the rear panel 22. The lateral stiffening elements 82 and 84 are created by regions of bonding between the rear panel 22 and the rear wall 4. The lateral stiffening elements 82 and 84 are arranged parallel with and spaced immediately adjacent the fold line C-C above and below the fold line C-C respectively. The stiffening elements 82 and 84 provide additional structure to the rear part 22 of the cover 20 that promote folding about the fold line C-C. The stiffening elements 82 and 84 may also be used independently of the notches 80,80b, as shown in the embodiment of FIG. 14.

The invention claimed is:

1. A collecting device such as an ostomy pouch or wound bag comprising:
   a collecting bag for containing bodily fluids or waste matter;
   an opening in the collecting bag for receiving the bodily fluids or waste matter;
   a flexible material cover at least partially covering the collecting bag, the cover comprising a front part arranged on a first side of the collecting bag that in use faces forward away from the wearer;
   wherein the front part of the cover includes a lower panel section located at a lower end of the collecting device having an upper end comprising a cut away section shaped to form a viewing window through which the opening is visible and an upper panel section located at an upper end of the collecting device that is reconfigurable between a closed configuration in which at least part of the upper panel section covers the viewing window and the opening is obscured, and an open configuration in which the viewing window is uncovered and the opening is visible.

2. The collecting device according to claim 1, further comprising a holding means arranged to hold the upper panel section in the open configuration.

3. The collecting device according to claim 2, wherein the upper panel section comprises a flap portion and the holding means comprises a retaining slit located at the lower end of the flap portion that is arranged to receive part of the upper edge of the device when the flap portion is in the open configuration to hold the flap portion in the open configuration.

4. The collecting device according to claim 3, further comprising a locking tab projecting from the upper end of the pouch and the retaining slit and the locking tab are configured and arranged such that the locking tab is able to be inserted through the slit when the flap portion is in the open configuration to hold the flap portion in the open configuration.

5. The collecting device according to claim 1, wherein the opening is located towards the upper end of the pouch.

6. The collecting device according to claim 1, wherein the collecting bag comprises a front wall and rear wall formed of a flexible polymeric material, and wherein at least the front part of the cover and the front and rear walls of the collecting bag are bonded together along their peripheral edges.

7. The collecting device according to claim 6, wherein the pouch further comprises a mounting plate having a front surface bonded to the rear wall of the collecting bag in a bonding region, wherein the viewing window is configured such that the stoma opening and the bonding region are visible therethrough.

8. The collecting device according to claim 1, wherein at least part of an outer peripheral edge of the upper panel section is bonded to the collecting bag and the upper panel section includes a flap portion that is movable between the open and closed configurations.

9. The collecting device according to claim 8, wherein the lower panel section has an upper edge that extends across the collecting bag and is shaped to form the viewing window.

10. The collecting device according to claim 9, wherein the upper edge comprises a curved cut away section that forms the viewing window, the curved cut away section having a concave substantially semi-circular shape.

11. The collecting device according to claim 10, wherein the lower panel section is bonded to the collecting bag around its peripheral edge defining a lower bonding seam, and the upper panel section is bonded to the collecting bag around the outer peripheral edge defining an upper bonding seam, and upper ends of the lower bonding seam and lower ends of the upper bonding seam are immediately adjacent each other.

12. The collecting device according to claim 11, wherein the lower ends of the upper bonding seam of the upper panel section and the upper ends of the lower bonding seam of the lower panel section are located adjacent and below the lower ends of lower bonding seam, and a point at which the upper and lower ends meet defines outer ends of a fold line about which the flap portion of the upper panel section is foldable to move between the open and closed configurations.

13. The collecting device according to claim 12, wherein in the closed configuration the flap portion of the upper panel extends downwardly below the fold line and at least partially overlaps the lower panel section.

14. The collecting device according to claim 13, wherein:
the flap portion tapers inwardly in a downward direction in the closed configuration; and/or
the fold line of the flap is located above the stoma opening.

15. The collecting device according to claim 14, wherein the cutaway section of the lower panel section curves convexly downwards away from the fold line.

16. The collecting device according to claim 1, wherein the upper panel section has a lower edge that is lowermost in the closed configuration and the upper panel section includes a strengthening zone located along the lower edge to strengthen the lower edge and maintain a form of the upper panel section in use.

17. The collecting device according to claim 16, wherein the upper panel section includes inner and outer flexible material panels and an intermediate flexible polymer film that are bonded together to form the strengthening zone along the lower edge of the upper panel section.

18. The collecting device according to claim 17, wherein the lower panel section includes a flap portion, the lower edge forms part of the flap section and the strengthening zone extends along the lower edge supports the flap section in the open configuration.

19. The collecting device according to claim 1, wherein the upper panel section includes a flap portion having an inner side that faces towards the collecting bag in the closed configuration and wherein a first fastener is located at a lower end of a rear part of the cover and a corresponding second fastener is located on the inner side of the flap, and the pouch is foldable to a compact configuration in which the lower end of the rear part is located beneath the flap portion of the front part and the first and second fasteners are configured to hold the pouch in the compact configuration.

20. The collecting device according to claim 7, wherein the bonding region between the mounting plate and the collecting bag is circular and the semi-circular cut away section has a radius corresponding to a radius of the bonding region, such that the semi-circular edge of the cut away is aligned with an outer edge of the bonding region.

* * * * *

UNITED STATES PATENT AND TRADEMARK OFFICE
CERTIFICATE OF CORRECTION

PATENT NO. : 12,329,674 B2
APPLICATION NO. : 17/800792
DATED : June 17, 2025
INVENTOR(S) : Benjamin Derek Mahood, Nathan Brennan and Sebastian Miller Page 1 of 1

It is certified that error appears in the above-identified patent and that said Letters Patent is hereby corrected as shown below:

On the Title Page

Item (72), inventor 1, city, delete "Comber County Down (GB)" and insert --Comber County Dow (GB)--, therefor.

Item (72), inventor 2, city, delete "Comber County Down (GB)" and insert --Comber County Dow (GB)--, therefor.

Item (72), inventor 3, city, delete "Comber County Down (GB)" and insert --Comber County Dow (GB)--, therefor.

Signed and Sealed this
Thirteenth Day of January, 2026

John A. Squires
*Director of the United States Patent and Trademark Office*